United States Patent [19]

Srnka et al.

[11] Patent Number: 5,053,406

[45] Date of Patent: Oct. 1, 1991

[54] COMPOSITIONS AND METHODS FOR PREVENTING AND TREATING ROTAVIRAL INFECTIONS

[75] Inventors: Cherly Srnka; Roger A. Laine, both of Alameda; James Gilbert, Oakland, all of Calif.

[73] Assignee: Glycomed, Inc., Alameda, Calif.

[21] Appl. No.: 450,198

[22] Filed: Dec. 13, 1989

[51] Int. Cl.$^5$ .............................................. A61K 31/575
[52] U.S. Cl. ..................................................... 514/182
[58] Field of Search ........................................... 514/182

[56] References Cited

FOREIGN PATENT DOCUMENTS 0034835  9/1981  European Pat. Off. .

OTHER PUBLICATIONS

Yolken et al., *J. Clin. Invest.* (1987) 79:148-154.
Willoughby et al., *Abstracts of the Proceedings of U.S-.-Japan International Rotavirus Meeting*, Anapolis, Md. (Aug. 1989).
Lecce et al., *Infect. Immunol.* (1976) 14:816-825.
Mebus et al., *Infect. Immunol.* (1976) 14:471-474.
Wyatt et al., *Science* (1980) 207:189-191.
Jetten et al., *J. Invest. Dermatol.* (1989) 92:203.
Nichols et al., *J. Lipid Res.* (1988) 29:1205.

*Primary Examiner*—Shep K. Rose
*Attorney, Agent, or Firm*—Irell & Manella

[57] ABSTRACT

Compositions useful in the prevention and treatment of rotaviral infections are disclosed. The subject compositions contain cholesterol 3-sulfate or functional derivatives thereof. Cholesterol 3-sulfate avidly binds rotavirus in thin layer overlay assays and inhibits rotavirus in plaque reduction assays. These compositions can be used to prevent and ameliorate rotaviral infections.

5 Claims, 1 Drawing Sheet

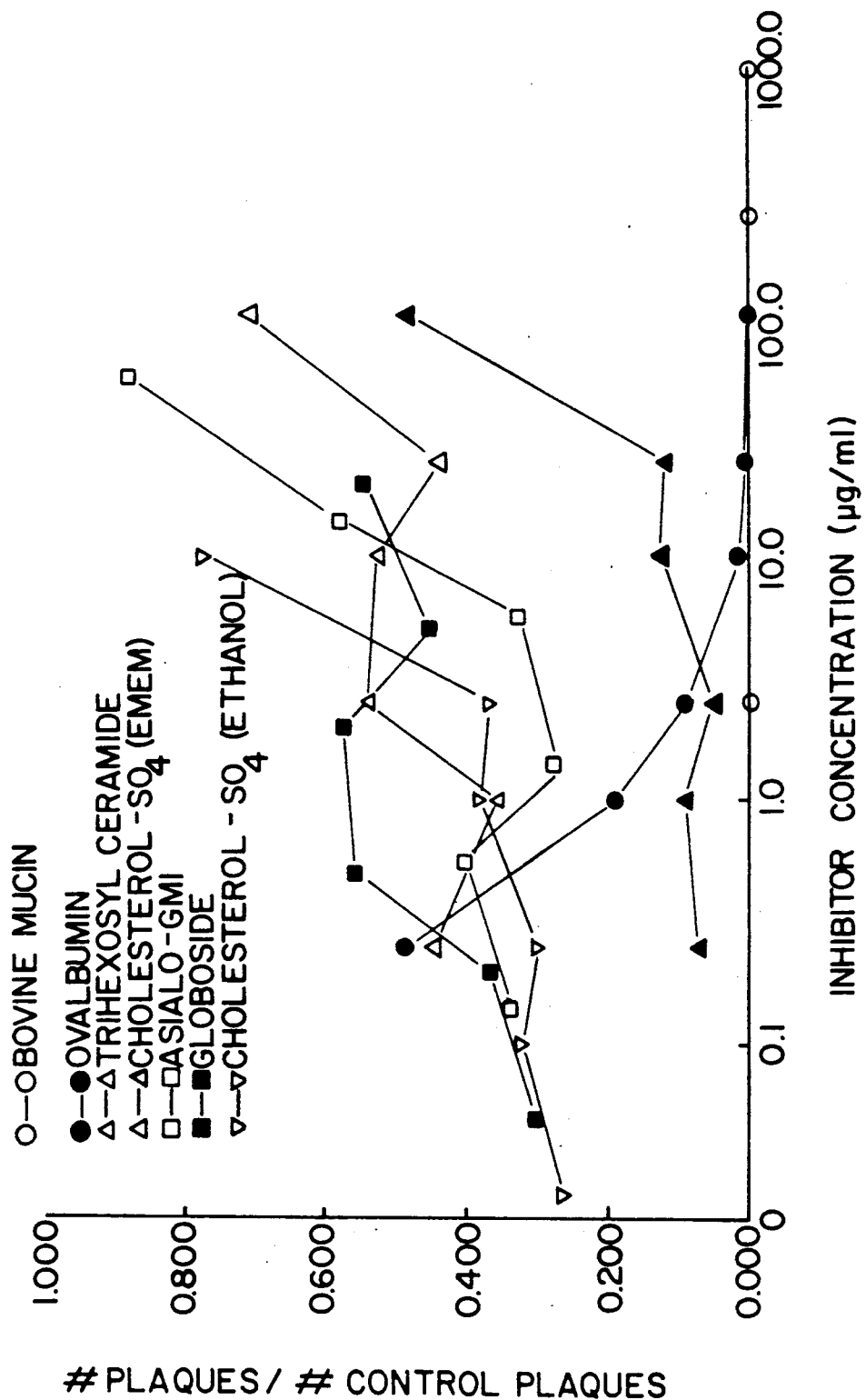

COMPOSITIONS AND METHODS FOR PREVENTING AND TREATING ROTAVIRAL INFECTIONS

TECHNICAL FIELD

The instant invention relates generally to compositions and methods for treating viral infections. More specifically, the subject invention relates to the use of cholesterol 3-sulfate and functional derivatives thereof in the prevention and treatment of rotavirus induced diseases.

BACKGROUND OF THE INVENTION

Rotaviruses are double stranded RNA viruses of the family Reoviridae. These viruses replicate in the intestinal epithelial cells of a wide range of animal species including most mammalian and avian species and are the major etiological agents of several gastrointestinal disorders in humans and other animals. For example, rotaviruses are responsible for infantile diarrhea and enteritis, causing infant morbidity and mortality. Rotaviruses also cause diarrhea illnesses in calves and piglets, as well as other mammals. These viruses are responsible for debilitating diarrhea in immune-compromised patients such as transplant recipients and AIDS sufferers and have been implicated as a significant cause of traveler's diarrhea. Currently, there is no effective prophylactic or therapeutic drug available to combat rotaviral disorders and attempts to develop vaccines have been problematic.

In order to infect cells and replicate, viruses bind specific receptors on the target cell surface. After attachment, the virus fuses with the cell membrane and is internalized where it uses the target cell's own metabolism to replicate. The initial attachment process is therefore essential to successful infection.

The details of the initial interaction between rotaviruses and the host cell surface have not been completely elucidated. However, sialic acid appears to be an important component of the rotavirus receptor, Yolken et al., J. Clin. Invest. 79: 148-154 (1987), and asialo GM1 binds rotavirus and inhibits viral replication in plaque reduction assays. Willoughby et al., abstract from Proceedings of U.S.-Japan International Rotavirus Meeting, Anapolis, Md. August 1989. Furthermore, bovine submaxillary mucin and chicken ovoinhibitor have been shown to prevent rotavirus gastroenteritis in mice. Yolken et al., supra. Additionally, it has been shown that rotavirus strains isolated from one species cross-react with hosts of another species (see e.g. Leece et al., Infect. Immun. 14: 816-825 (1976); Mebus et al., Infect. Immun. 14: 471-474 (1976); Wyatt et al., Science 207: 189-191 (1980)), suggesting conservation of rotaviral receptors between species.

Molecules able to interact with rotavirus or target cell rotaviral binding proteins could be used as antiviral agents to prevent the subsequent infection of host cells. A distinct advantage of such an approach over traditional methods of preventing viral infections, e.g. vaccines, is that the portion of the viral protein normally binding to the specific cell surface carbohydrate does not mutate. Thus, antiviral agents which act by preventing viral binding are likely to remain effective in the face of mutations to other parts of the viral genome.

Cholesterol 3-sulfate is a lipid constituent of mammalian plasma membrane and has the following structure.

Cholesterol 3-Sulfate

This substance is particularly noted in epithelial cells during differentiation. Jetten et al., J. Invest. Dermatol. 92: 203 (1989). Cholesterol 3-sulfate has been postulated to relate to polarity of cell growth in tissue culture. Nichols et al., J. Lipid Res. 29: 1205 (1988).

SUMMARY OF THE INVENTION

The present invention is based on the discovery that cholesterol 3-sulfate avidly binds rotavirus, thus preventing the subsequent interaction of the virus with the target cell. Furthermore, this substance effectively inhibits rotavirus in plaque reduction assays. Cholesterol 3-sulfate or functional derivatives thereof can be advantageously employed to prevent or treat rotaviral infections.

In one embodiment, the present invention is directed to a composition for preventing or treating rotaviral infection comprising a therapeutically effective amount of cholesterol 3-sulfate or a functional derivative thereof in combination with a pharmaceutically acceptable carrier.

In yet another embodiment of the subject invention, a method for preventing or treating rotavirus induced disorders is disclosed. The method comprises administering to a subject a therapeutically effective amount of cholesterol 3-sulfate or a functional derivative thereof.

In particularly preferred embodiments, the cholesterol 3-sulfate is administered orally, linked to an inert support.

Further embodiments of the present invention will, readily occur to those of ordinary skill in the art.

BRIEF DESCRIPTION OF THE FIGURES

FIG. 1 depicts the results of a plaque reduction assay with cholesterol 3-sulfate using globoside as a negative control and ovalbumin and bovine mucin as positive controls.

DETAILED DESCRIPTION

A. General Methods

Central to the instant invention is the discovery that cholesterol 3-sulfate is capable of binding rotavirus in overlay thin layer chromatography assays and that this substance inhibits rotavirus as determined in plaque reduction assays (both described more fully below). Cholesterol 3-sulfate is readily available commercially (Sigma) or can be isolated from mouse small intestine cells using a modified Folch extraction as developed by Svennerholm and Fredman, Biochim. Biophys. Acta 617: 97-109 (1980), the disclosure of which is incorporated by reference herein in its entirety. This isolation method is described in detail in the experimental section.

Cholesterol 3-sulfate was able to bind labeled rotavirus in overlay thin layer chromatography assays, and was shown to inhibit rotavirus in vitro in standard plaque reduction assays.

Cholesterol 3-sulfate or a functional derivative thereof can be administered to a subject either prohylactically or after rotaviral infection. By "functional derivative" of cholesterol 3-sulfate is meant a compound structurally similar to cholesterol 3-sulfate which retains biological activity as determined by rotavirus binding assays and plaque reduction assays described herein.

The compositions of the present invention can be administered with a pharmaceutically acceptable carrier, the nature of the carrier differing with the mode of administration. For example, oral administration, the method of choice, can be accomplished using a variety of excipients including, for example, pharmaceutical grades of mannitol, lactose, starch, magnesium, stearate, sodium saccharin cellulose, magnesium carbonate, and the like. These oral compositions may be taken in the form of solutions, suspensions, tablets, pills, capsules, sustained release formulations, or powders. Particularly useful is the administration of cholesterol 3-sulfate directly in infant nutrient formulae or rehydration formulae, given to replenish electrolytes lost in severe bouts of diarrhea.

Alternatively, the compositions of the instant invention can be administered orally, linked to inert supports such as beads, resins, or natural or synthetic polymers. Methods for binding substances to such supports are well known in the art. Cholesterol 3-sulfate may also be administered in small lipid particles comprising the subject glycolipids, such as in vesicles, micelles, or liposomes.

A therapeutically effective amount of cholesterol 3-sulfate should be administered to bind to a substantial portion of the rotavirus expected to cause or actually causing infection so that infection can either be prevented or ameliorated. By "therapeutically effective amount" is meant the amount of cholesterol sulfate sufficient to prevent, i.e. prophylactically, or treat, i.e. reduce or eliminate the symptoms of rotavirus induced disorders, in a recipient subject when administered in the composition of the invention.

Typically, the oral compositions of the instant invention will contain from about 10% to about 95% of the active ingredient, preferably about 25% to about 70%. Preferably, between about 12 ug and 1.2 mg will be administered to a child and between about 200 ug and 10 mg will be administered to an adult. Other effective dosages can be readily determined by one of ordinary skill in the art through routine trials establishing dose response curves.

Other modes of administration will also find use with the subject invention. For instance, cholesterol 3-sulfate can be formulated in suppositories and, in some cases, aerosol and intranasal compositions. For suppositories, the vehicle composition will include traditional binders and carriers such as, polyalkaline glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

The compositions of the instant invention may also be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles. The cholesterol 3-sulfate can be mixed with compatible, pharmaceutically acceptable excipients. Suitable vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of cholesterol 3-sulfate adequate to achieve the desired state in the subject being treated.

B. Experimental

Below are examples of specific embodiments for carrying out the present invention. The examples are offered for illustrative purposes only, and are not intended to limit the scope of the present invention in any way.

EXAMPLE 1

Isolation of Cholesterol 3-Sulfate from the Mouse Intestine

Cholesterol 3-sulfate was isolated from mouse small intestine in the following manner. Adult Swiss mice (obtained from Bantin and Kingman, Fremont, Calif.) were sacrificed by $CO_2$ asphyxiation and the small intestine removed, washed, and homogenized in distilled water (3 ml/g tissue) using a Waring blender. 8 ml of methanol per gram of tissue was added and blended. 4 ml of chloroform per gram of tissue was then added and the tissue extracted for 3 hours. The extract was vacuum filtered through a bed of Celite supported on a glass fiber pad to remove the insoluble residue. Distilled water was added to the collected extract to achieve a final chloroform:methanol:water ratio of 4:8:3 (v:v:v). After mixing, the extract was allowed to partition overnight, and the lower, aqueous phase containing the more polar lipids removed and concentrated until dry by rotary and speed vacuum evaporation at 45° C. The sample was suspended in distilled water by sonication, extensively dialyzed, lyophilized and redissolved in chloroform:methanol:water (4:8:3 v:v:v). The dissolved sample was fractionated on a DEAE fast flow Sepharose anion exchange column using a gradient of sodium acetate in methanol. Putative cholesterol 3-sulfate eluted from this column with 10 to 20 mM sodium acetate in methanol.

The putative cholesterol 3-sulfate containing fractions were concentrated by speed vacuum evaporation and dialyzed and lyophilized. The sample was dissolved by sonication in chloroform:methanol, 98:2 (v:v), and the lipids in the sample were fractionated according to polarity on a normal phase column (Iatrobead or silica) using a step gradient from 98:2 chloroform:methanol (v:v) to chloroform:methanol:water, 55:45:10 (v:v:v). The putative cholesterol 3-sulfate eluted in chloroform-:methanol 9:1 to 8:1 (v:v).

This lipid was shown to comigrate with commercially purchased cholesterol 3-sulfate (from Sigma) on silica thin layer plates and had an Rf of 0.9 relative to lactosyl ceramide using chloroform:methanol:0.25% aqueous KCl as a solvent. This substance stained a blue-purple color with resorcinol and with orcinol spray reagents and was not degraded by mild base treatment which is sufficient to degrade phospholipids (0.1N NaOH, in methanol for three hours at 37° C.) but was degraded by hydrolysis for two hours in 0.1N HCl at 80° C. The isolated lipid was confirmed to be cholesterol 3-sulfate by mass spectrometry and gas chromatography.

EXAMPLE 2

Rotavirus Thin Layer Overlay Binding Assay

The ability of cholesterol 3-sulfate to bind rotavirus was tested in the following manner.

Rotavirus SA11 for use in the following experiment was grown in and isolated from MA104 cells, available from Whittaker Bioproducts, Walkersville Md., using previously described methods. See, e.g. Yolken et al., J. Clin. Invest. 79: 148–154 (1987) and Kabcenell et al., J. Virol. 62: 2929 (1988), the disclosures of which are incorporated herein by reference in their entirety. The virus was iodinated using solid state iodobeads as reagent as described by Markwell, M. A., Analyt. Biochem. 125: 427–432 (1982), incorporated herein by reference. Approximately 25 ug of gradient purified virus (by protein assay) were incubated with 2 mCi of Na $^{125}$I and the virus subsequently purified by gel exclusion on a PD-10 column.

Silica 60 high performance thin layer chromatography plates (Merck) were spotted with cholesterol 3-sulfate and from 50 to 500 pmoles of asialo GM1 as standard. The plates were run in chloroform:methanol:water 60:40:10 (v:v:v). The plates were probed with $10^7$ dpm of $^{125}$I-labeled rotavirus per 100 sq.cm. using a modification of the technique of Magnani et al., Anal. Biochem. 109: 399–402 (1980).

After probing, the plates were treated with iodine and sprayed with orcinal (Alltech). Approximately 0.1 to 0.5 ug of cholesterol 3-sulfate was sufficient to bind $^{125}$-I-labeled rotavirus.

EXAMPLE 3

Rotavirus Plaque Reduction Assay

The ability of cholesterol 3-sulfate to inhibit rotavirus infection was tested in vitro using the following plaque reduction assay. SA11 rotavirus (at 100 pfu) was added to 6 well plates containing confluent MA104 cells. The cells were incubated for one hour at, 37° C., the inoculum removed and the cells washed once with EBSS medium. The cells were overlaid with 3 mls of medium containing 0.7% agarose and cholesterol 3-sulfate (Sigma). Also tested were other inhibitors of rotavirus including asialo GM1, globoside, and trihexosyl ceramide. Ovalbumin and bovine submaxillary mucin were added as positive controls. The overlay was allowed to gel after which the plates were incubated for 48 hours and the number of plaques counted. As can be seen in FIG. 1, cholesterol 3-sulfate significantly reduced plaque formation when compared to untreated controls.

Thus, compositions and methods useful in the prevention and treatment of rotavirus infection have been disclosed. Although preferred embodiments of the subject invention have been described in some detail, it is understood that obvious variations can be made without departing from the spirit and the scope of the invention as defined by the appended claims.

We claim:

1. A method for preventing or treating rotaviral infection comprising administering to a subject in need thereof a therapeutically effective amount of cholesterol 3-sulfate in combination with a pharmaceutically acceptable carrier.

2. A method of preventing or treating rotaviral infection comprising administering to a subject in need thereof a therapeutically effective amount of cholesterol 3-sulfate linked to an inert support.

3. The method of claim 1 wherein said composition is administered orally.

4. The method of claim 2 wherein said composition is administered orally.

5. A method of preventing or treating rotaviral infection comprising orally administering to a subject in need thereof a therapeutically effective amount of cholesterol 3-sulfate linked to an inert support.

* * * * *